United States Patent [19]

Johnson et al.

[11] Patent Number: 5,235,988
[45] Date of Patent: Aug. 17, 1993

[54] DEVICE FOR EVALUATING SURFACE CONTOUR

[75] Inventors: David S. Johnson, Stamford; Alfred G. Evans, Torrington, both of Conn.

[73] Assignee: United States Surgical Corporation, Norwalk, Conn.

[21] Appl. No.: 731,125

[22] Filed: Jul. 15, 1991

[51] Int. Cl.⁵ ............................................. A61B 5/103
[52] U.S. Cl. .................................... 128/774; 33/512; 33/836
[58] Field of Search ........................ 128/774; 606/102; 33/512, 511, 513, 514.1, 514.2, 515, 836, 1 E, 1 H, 8, 122, 719, 720, 501.07, 501.09, 521, 624, 625, 542, 544, 544.6, 559, 571, 572, 573

[56] References Cited

U.S. PATENT DOCUMENTS

| | | | |
|---|---|---|---|
| 92,773 | 7/1869 | Archibald | 33/1 H |
| D. 254,656 | 4/1980 | Suwa . | |
| D. 268,911 | 5/1983 | Gordon . | |
| D. 271,184 | 11/1983 | Gentry . | |
| D. 277,557 | 2/1985 | Lenceski . | |
| 1,248,340 | 11/1917 | Kinney | 33/836 |
| 2,373,338 | 7/1942 | Rakauskas | 33/485 |
| 2,654,156 | 2/1952 | Boyer | 33/836 |
| 2,705,840 | 2/1954 | Keppler et al. | 33/720 |
| 2,763,935 | 9/1956 | Whaley et al. . | |
| 2,893,130 | 5/1957 | Ierokomos | 33/544 |
| 3,128,559 | 12/1960 | Winter | 33/544 |
| 3,269,019 | 2/1965 | Krohn | 33/836 |
| 3,478,435 | 3/1968 | Cook | 33/511 |
| 3,738,355 | 6/1973 | Salvatore | 33/512 |
| 3,821,854 | 7/1974 | Koch et al. | 33/544 |
| 3,945,122 | 3/1976 | Durand et al. | 33/512 |
| 4,005,527 | 2/1977 | Wilson et al. . | |
| 4,165,566 | 8/1979 | Lycan | 33/542 |
| 4,233,979 | 11/1980 | Naser . | |
| 4,279,260 | 7/1981 | Stump | 128/774 |
| 4,321,752 | 3/1982 | Kaufman | 33/512 |
| 4,483,075 | 11/1984 | Kundin | 33/512 |
| 4,566,466 | 1/1986 | Ripple et al. | 128/781 |
| 4,613,324 | 9/1986 | Ghajar . | |
| 4,840,564 | 6/1989 | Segal | 433/72 |
| 4,894,920 | 1/1990 | Butler et al. | 33/203.11 |
| 4,931,056 | 6/1990 | Ghajar et al. . | |
| 4,998,938 | 3/1991 | Ghajar et al. | 606/130 |

FOREIGN PATENT DOCUMENTS 2497655 7/1982 France ................... 128/774

*Primary Examiner*—Max Hindenburg
*Assistant Examiner*—Guy V. Tucker
*Attorney, Agent, or Firm*—Thomas R. Bremer; Peter G. Dilworth; Rocco S. Barrese

[57] ABSTRACT

A device for evaluating the surface contour of various body parts which may measure surface elevation or depth of depressions and cavities. The device includes a body portion having a plurality of legs extending downwardly to position the device on a body part such as the skull. A slidable member having a calibrated scale thereon is positioned in a slot in the body of the device. An indexer is provided to indicate the distance the slidable member moves so that surface elevations or depressions may be evaluated.

12 Claims, 6 Drawing Sheets

DEVICE FOR EVALUATING SURFACE CONTOUR

BACKGROUND OF THE INVENTION

1. Field Of The Invention

The present invention relates to surgical instruments for evaluating the surface contour of the body, and more particularly to devices for evaluating the surface contour of body parts such as the skull for cosmetic purposes following surgery.

2. Discussion Of The Prior Art

Surgical devices for measuring thickness and depth of body tissue are well known in the art. These devices typically include a sliding scale which can measure depth of body cavities or the thickness of tissue by positioning the device on the surface to be measured and sliding a calibrated member through the body cavity or moving the member to pierce the tissue. Several prior art devices provide a rotatable member which moves a calibrated bit to measure depth. Several other devices provide a piercing member to puncture tissue to measure the thickness on a sliding scale.

The prior art measuring devices are subject to several disadvantages during use which render the devices inaccurate in most applications, and in some instances preclude measurement of surface elevations. Many of the known devices require that the reference point at which a movable calibrated member is initially extended be flush with a flat area of tissue or bone. In many instances the surgeon's view is obstructed by the reference member so that an inaccurate indication of depth is obtained. Furthermore, many devices require the application of pressure which compresses the tissue and renders an inaccurate reading of depth or thickness.

Due to the construction of the known devices, accurate measurement of surface elevations is virtually impossible, so that the devices only can measure depth of surgically created body cavities. In cosmetic applications, such as plastic surgery in which the height of a scar must be accurately assessed to aid the surgeon in eliminating the unsightly scar tissue, the height of the scar tissue must be precisely determined. In addition, certain surgical procedures, such as brain surgery, require the accurate measurement of the bore hole through the cranium so that the exact amount of filler material may be applied to close the hole in the skull. While many of the devices of the prior art may be used to estimate the depth of a cranial bore hole, none of these devices may be used to determine the surface elevation after the hole has been filled, to aid the surgeon in smoothing over the filler material to eliminate uneven cosmetic appearance.

Typical of the prior art devices is the measuring device disclosed in U.S. Pat. No. 3,478,435 to Cooke, which provides a depth gauge for measuring the thickness of animal tissue. This device includes a calibrated scale upon which is mounted a reference member which engages the surface of the skin of the animal. A piercing member is provided on an indicator device which is slidable over the scale member. As the rod pierces the tissue, the thickness of the tissue can be measured with reference to the scale.

U.S. Pat. No. 3,738,355 to Salvatore and U.S. Pat. No. 4,566,466 to Ripple et al. disclose measuring devices for evaluating the thickness of bones. Salvatore discloses a bone gauge which measures the thickness or diameter of a bone and includes a rotatable body which extends wire hooks which pass through the bone to engage the far side of the bone to allow for a reading of the thickness or diameter of the bone. Ripple et al. provides a device which allows for the determination of the depth of cavities in bones such as that between vertebrae.

U.S Design Pat. No. 254 656 to Suwa and U.S. Design Pat. No. 268,911 to Gordon disclose depth measuring micrometers which must be placed flat on the surface adjacent the cavity whose depth is to be measured so that the bit member may be rotated into the cavity to determine the depth.

The devices found in the prior art are primarily directed to depth measuring devices which in many times obstruct the view of the surgeon and may lead to inaccurate measurement of depth or thickness. Furthermore, many of the devices of the prior art are complex mechanical devices which are precision instruments and which are expensive and complex to manufacture. Furthermore, the prior art devices preclude accurate measurement of surface elevations and thus are not practical for use in cosmetic surgery.

The novel surface contour evaluating device of the present invention obviates the disadvantages encountered in the prior art and provides a simple and accurate device for use in evaluating the surface contour of parts of the body which can measure surface depressions, cavities, for elevations to aid a surgeon during the surgical procedure. The device of the present invention allows a surgeon to accurately assess surface elevations during cosmetic surgery such as the removal of scar tissue, as well as to evaluate depressions or cavities in bone structure during surgical procedures such as brain surgery. An accurate indication of the depth of a bore hole allows the surgeon to determine the amount of filler material necessary to fill the cranial bore hole, and also allows the surgeon to evaluate surface elevations after the hole has been filled to assist in correction of cosmetic appearance. The device is easy to manufacture and assemble, and gives a quick and accurate visual indication of the height or depth of the surface contour.

SUMMARY OF THE INVENTION

The present invention provides a novel measuring device for evaluating the surface contour of body parts which is operable to measure both surface elevation and the depth of surface cavities or depressions in the body. The device includes a body portion having a plurality of legs extending downwardly from a face portion which serves as the reference point for measuring distance. Preferably, the body portion includes at least three legs which provides an unobstructed view for the surgeon to determine contact with tissue to prevent compressing the tissue which would result in an inaccurate measurement.

The face portion of the present device includes a slot through which a calibrated slidable member passes which includes a surface engaging tip to provide an indication of the height of surface elevations or the depth of surface cavities or bore holes. At least one upwardly directed projection extends from the face portion and includes an indicator which aligns with the scale of the calibrated member to indicate height or depth.

In use, the device is placed on the surface of the body at the location of a surface elevation or depression, such as a bore hole in the skull following brain surgery. The legs of the device straddle the hole and the calibrated member is set at its initial or zero position. As the calibrated member is moved downwardly, the surgeon can visually see the tip of the calibrated member engage the tissue within the bore hole at which time the sliding movement is stopped. A scale on the calibrated member indicates depth of the hole so that the surgeon may determine the amount of filler material necessary to fill the hole. After the filler material hardens, a surgeon may then take another reading to determine if additional filler material is necessary, or if the filler material exceeds the plane of the skull, the surgeon has an accurate indication of the amount of material that must be removed to provide a smooth cosmetic appearance.

The present invention may also be used in cosmetic surgery or plastic surgery to determine the amount of scar tissue that must be removed to eliminate an unsightly scar. In addition, surface elevations may be measured using the present device to assist in cosmetic surgical procedures to allow the surgeon to have an accurate indication of the amount of bone material, cartilage material or skin that must be removed or filled to complete the cosmetic surgical procedure.

Accordingly, it is an object of the present invention to provide a device for evaluating surface contour which provides an indication of the surface elevations as well as depressions to determine height or depth.

It is a further object of the present invention to provide a device which allows a surgeon to measure depth of holes or cavities in the body in which the surgeon is provided with an unobstructed view during measurement.

It is another object of the present invention to provide a device for evaluating surface contour which is simple to manufacture and use.

It is yet another object of the present invention to provide a device for measuring depth of cranial holes to determine the amount of filler material necessary following brain surgery.

It is still another object of the present invention to provide a surface contour evaluating device to determine the height of surface elevations to assist in the determination of the amount of tissue or bone which must be removed during cosmetic or plastic surgery.

BRIEF DESCRIPTION OF THE DRAWINGS

The foregoing objects and other features of the present invention will become more readily apparent and may be understood by referring to the following detailed description of an illustrative embodiment of the novel device for evaluating surface contour, taken in conjunction with the accompanying drawings, in which.

DETAILED DESCRIPTION OF THE PREFERRED EMBODIMENTS

Figure 1:
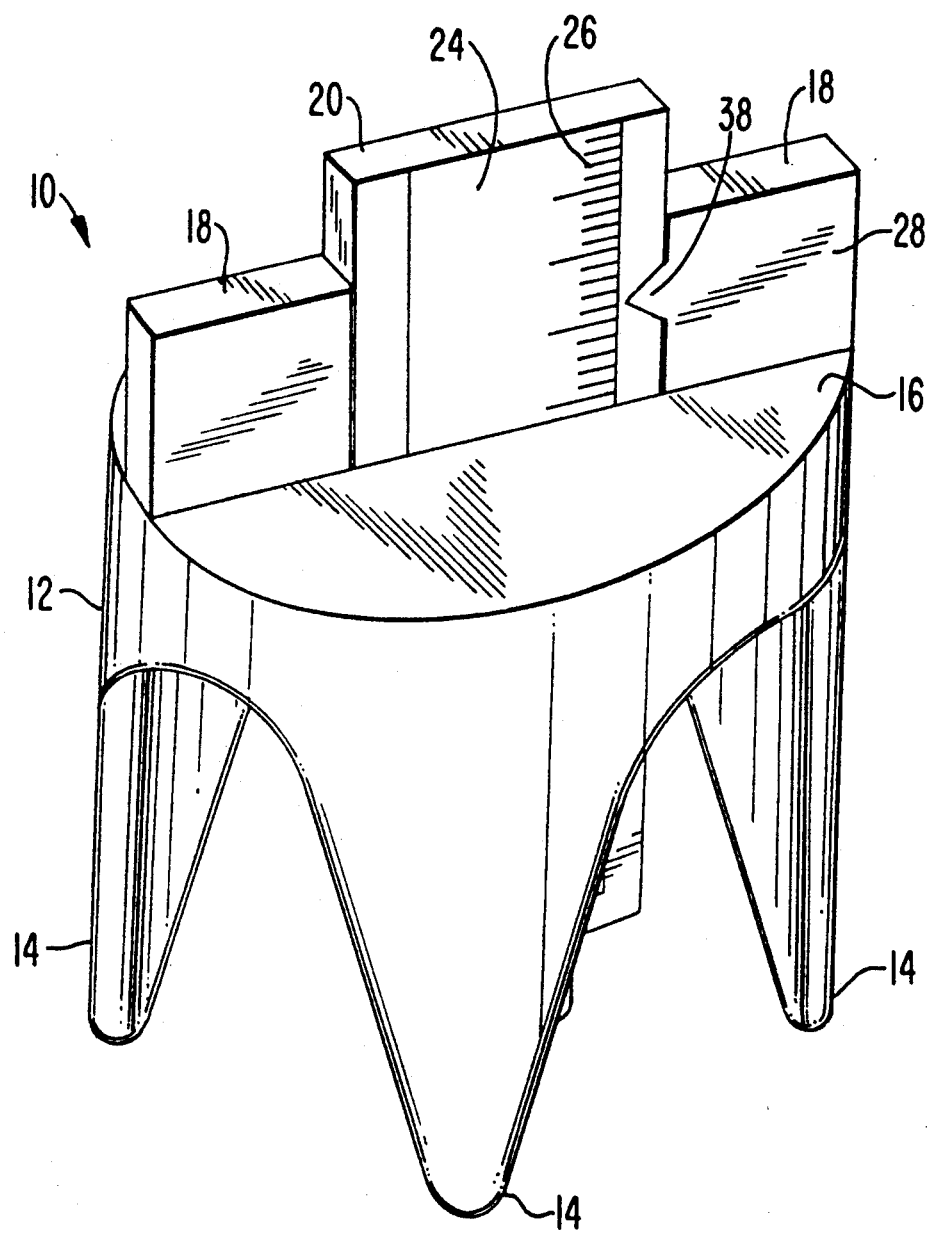
FIG. 1 illustrates a perspective view of the surface contour evaluating device of the present invention.

Referring now in specific detail to the drawings, in which like reference numerals identify similar or identical elements throughout the several views, FIG. 1 shows the surface contour evaluating device 10 of the present invention. The device 10 comprises a body portion 12 which may have any geometric shape, but in the preferred embodiment has a generally cylindrical shape as shown. A plurality of legs 14 extend downwardly to provide a means for resting the device 10 on a surface, such as the skull. It is expected that at least two legs be provided, but any number of legs may be employed, and in the preferred embodiment three legs are provided. It has been found that three legs are preferable in order to allow for measuring on curved surfaces such as the skull, and to minimize obstructing the surgeon's view during use.

Body portion 12 terminates in a face portion 16 which is generally perpendicular to legs 14. Two upstanding projections 18 are provided which assist in the measuring of height or depth as will be hereinafter described. It is apparent that only one projection 18 may be provided, and it is also contemplated that both projections may be eliminated so that body portion 12 terminates at face 16.

Calibrated member 20 is provided to give an indication of height or depth of the surface contour in which device 10 is used. Calibrated member 20 is slidingly secured in slot 22 provided in face 16 of device 10, and preferably is frictionally held in slot 22 to assure an accurate recordation of the measurement. Scale device 24 is provided in calibrated member 20 which is provided with calibrations 26 to perform the measurement. Preferably, the calibrations are in millimeters; however, it is clear that any scale could be utilized. As seen in FIG. 1, the scale may be unmarked, or may be numerically graded, as in FIG. 4. In addition, a "zero" line, such as transparent cursor, may be provided to assist in measuring by providing a starting point or reference marking. An indicator device 28 having an indexer 38 is secured to one of upstanding projections 18 to provide an indication of measurement in cooperation with calibrations 26. Indicator 28 may be secured to projection 18 in any conventional manner, such as by adhesives, screws, rivets or the like. Alternately, if projections 18 are eliminated, and consequently index 28 is not used, edge 23 of slot 22 may comprise the indexer for indicating the distance traveled by member 20 to indicate height or depth.

Figure 2:
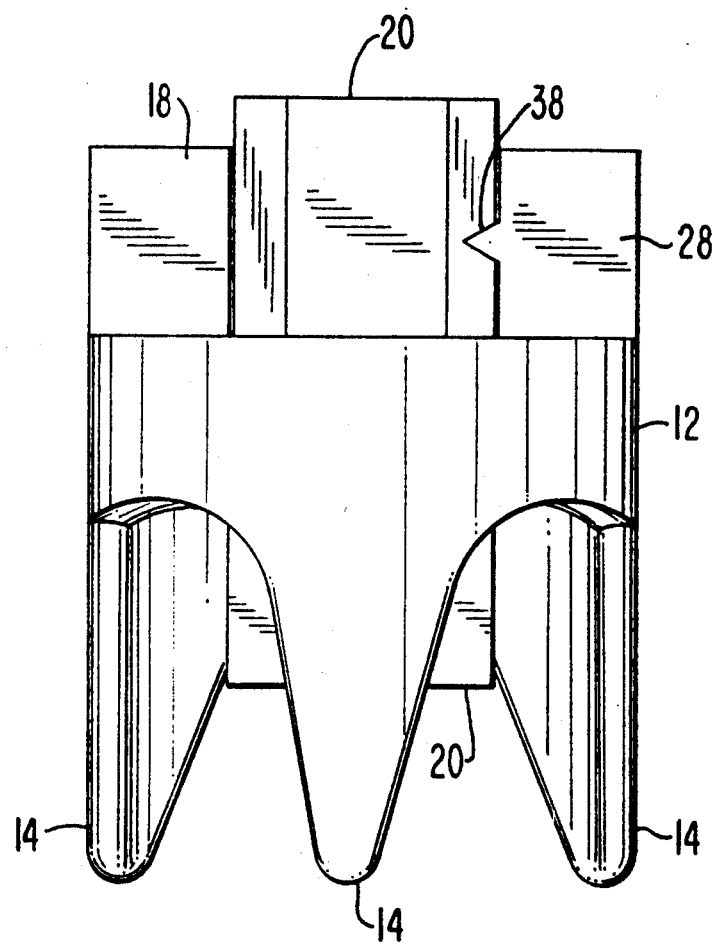
FIG. 2 illustrates a front plan view of the device of FIG. 1.
Figure 3:
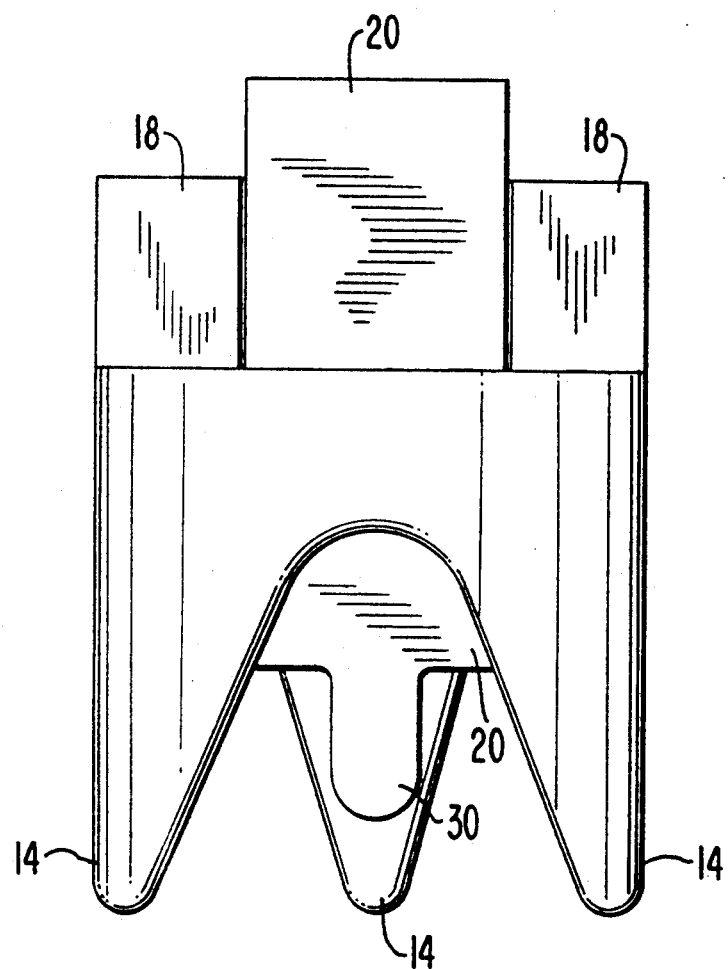
FIG. 3 illustrates a rear plan view of the device of FIG. 1.

As best seen in FIGS. 2 and 3, legs 14 extend downwardly from body portion 12 and rest on a surface whose surface contour is to be evaluated. Device 10 may be used to measure surface depressions or elevations, and in a preferred use is used to evaluate depth of cranial bore holes following surgery on the skull. To this end, legs 14 are placed on the skull to straddle the bore hole and calibrated member 20 is positioned at its initial starting point. As member 20 is pushed downwardly in a direction towards the skull, a tab member 30 extends into the bore hole while the surgeon may view its movement and subsequent contact with tissue through the spacings between legs 14. As tab 30 contacts tissue, the surgeon then may read on scale 24 the distance traveled by member 20 to determine the depth of the bore hole. The surgeon then may determine the amount of filler material necessary to close the hole. After the filler material has set, the surgeon may then use device 10 to determine if too much filler has been added or if more is necessary.

Device 10 may also be used in cosmetic or plastic surgery in that a surface elevation such as scar tissue may be evaluated to determine how much tissue must be removed during the procedure.

Figure 4:
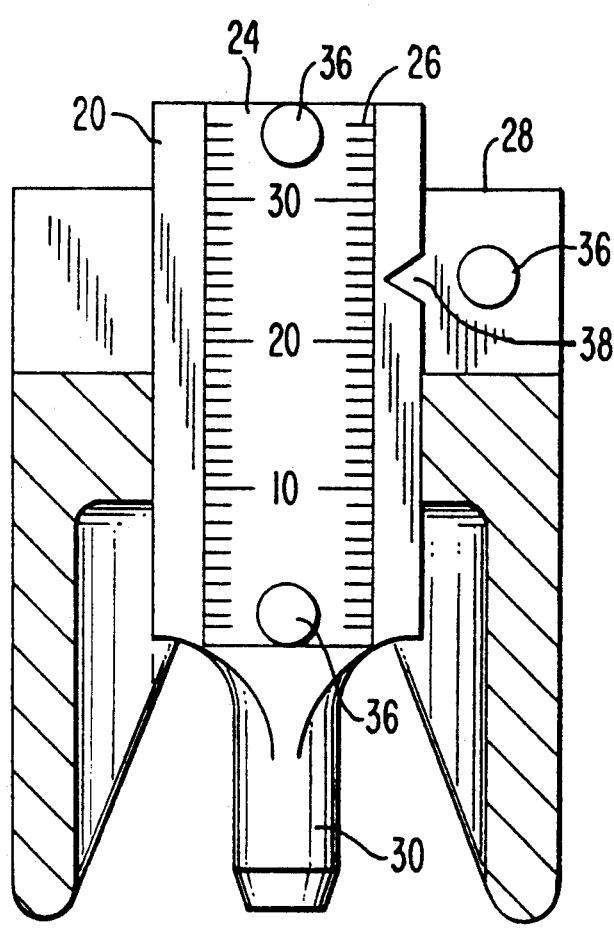
FIG. 4 illustrates a front plan view and partial cross section of the device of FIG. 1.

Turning now to FIG. 4, it is seen that scale 24 may be fastened to calibrated member 20 in a manner similar to the securement of indicator 28 to projections 18. As best seen in FIG. 4, fasteners 36, which may comprise screws, rivets, heat stakes, or the like are used to secure both the indicator and the scale to their respective positions. As also seen in FIG. 4, calibrations 26 may be marked in millimeters or any other suitable graduation. In addition, scale 24 may be eliminated and calibrations 26 may be printed directly on member 20.

Figure 5:
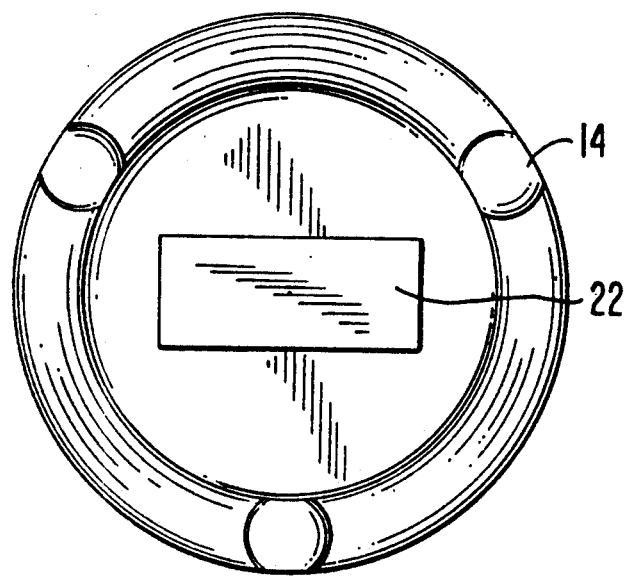
FIG. 5 illustrates a bottom plan view of the body portion of the device of the present invention.
Figure 6:
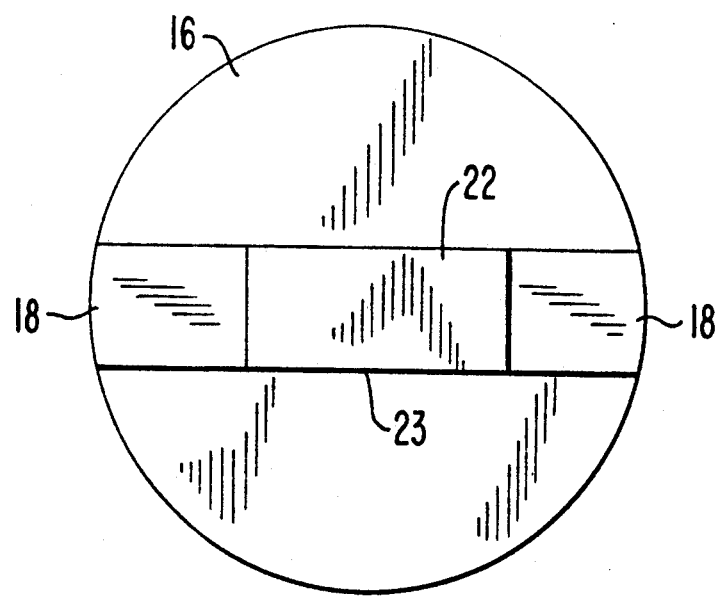
FIG. 6 illustrates a top plan view of the device of FIG. 5.

FIGS. 5 and 6 show the positioning of slot 22 in relation to legs 14 at face 16. As stated above, one or both projections 18, although shown in FIG. 6, may be eliminated in another embodiment.

Figure 7:
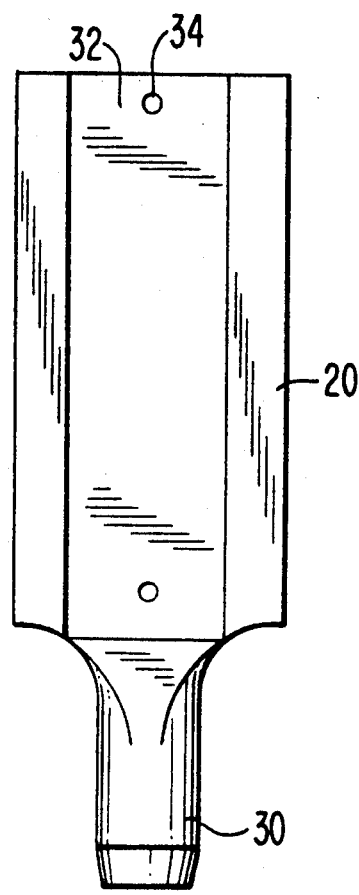
FIG. 7 illustrates a front plan view of the calibrated member of the present invention.
Figure 8:
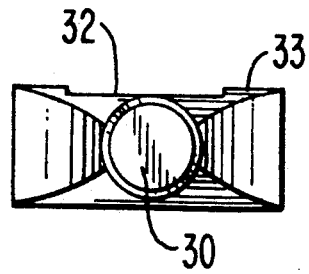
FIG. 8 illustrates a bottom plan view of the calibrated member of FIG. 7.

FIGS. 7 and 8 show calibrated member 20 without scale 24 positioned thereon. As best seen in FIG. 8, a slot or groove 32 is formed in calibrated member 20 to accept scale 24 so that the surface 33 maintains a common plane across its length when scale 24 is positioned thereon. Bore holes 34 are provided in one embodiment to secure scale 24 thereto.

The surface contour evaluating device of the present invention is preferably constructed of a plastic material which provides good sliding contact between the calibrated member and the slot formed in body portion 12. Preferably, the material used to form the device is a polyamide or nylon material, but of course any suitable material may be used. This device is simple to manufacture and use, and allows for the measurement of surface elevations as well as depressions or cavities using the single device.

While the invention has been particularly shown and described with reference to the preferred embodiment, it will be understood by those skilled in the art that various modifications and changes in form and detail be made therein without departing from the scope and spirit of the invention. Accordingly, modifications such as those suggested above, but not limited thereto, are to be considered within the scope of the invention.

What is claimed is:

1. A surgical device for measuring depth of a cavity in bone tissue, comprising:
    a body member having a face portion with a slot therein and at least three legs extending outwardly therefrom for supporting said device above said cavity in said bone tissue; and
    a calibrated member having calibrated indices provided thereon, said calibrated member being frictionally and slidably mounted on said body member, wherein said calibrated member is movable through said slot in relation to said body member in order to indicate depth of said cavity of said bone tissue.

2. A device according to claim 1, wherein said calibrated member is positionable with one end thereof in a plane with end portions of said legs, such that movement of said calibrated member in relation to said surface contour indicates depth of said surface contour.

3. A device according to claim 1, wherein said body member has a tripod shape wherein each of said at least three legs extends away from said body portion an equal distance.

4. A device according to claim 1, wherein said body member includes an indicator aligned with said calibrated member for providing a visual indication of distance said calibrated member moves to indicate depth of said surface contour.

5. A device according to claim 4, wherein said indicator comprises an upper edge of said body member.

6. A device according to claim 1, wherein said body member includes a face portion perpendicular to said legs and connecting each of said legs.

7. A device according to claim 1, wherein said seat is centered on said face portion.

8. A surgical device for measuring depth or height of surface contour of bone tissue, comprising:
    a body member having a face portion with a slot therethrough and legs extending therefrom;
    a calibrated member having calibrated indices provided thereon, said calibrated member being frictionally and slidably associated with said slot; and
    indicating means mounted on said body member for indicating distance traveled by said calibrated member to indicate height or depth of said bone tissue surface contour.

9. A device according to claim 8, wherein said face is perpendicular to said legs.

10. A device according to claim 9, wherein said indicating means comprises an edge of said face portion.

11. A surgical device for measuring height or depth of surface contour of bone tissue, comprising:
    a body member having a face portion and at least three legs extending perpendicularly from said face portion, said face portion having a slot therethrough; and
    a calibrated member having calibrated indices provided thereon, said calibrated member being frictionally and slidably movable through said slot, said calibrated member movable through said slot to indicate height or depth of said bone tissue surface contour.

12. A surgical device for measuring depth of a cavity in bone tissue, comprising:
    a body member having at least three legs extending away from a horizonal face portion, said face portion having a slot therethrough;
    a calibrated member having calibrated indices provided thereon, said calibrated member being frictionally and slidably mounted in said slot; and
    an indicator mounted on said body member to provide visual indication of said calibrated indices of said calibrated member;
    wherein said calibrated member is slidable in a direction towards said legs and away from said legs to determine depth of said bone tissue cavity.

* * * * *